US006274379B1

(12) United States Patent
Famodu et al.

(10) Patent No.: US 6,274,379 B1
(45) Date of Patent: Aug. 14, 2001

(54) PLANT SORBITOL BIOSYNTHETIC ENZYMES

(75) Inventors: Layo O. Famodu, Newark; Anthony J. Kinney, Wilmington, both of DE (US); Emil M. Orozco, West Grove, PA (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/347,803

(22) Filed: Jul. 2, 1999

Related U.S. Application Data
(60) Provisional application No. 60/092,952, filed on Jul. 15, 1998.

(51) Int. Cl.$^7$ .............................. C12N 15/00; C12N 9/04; A01H 1/00; C12Q 1/68; C07H 21/04
(52) U.S. Cl. .................. 435/440; 536/23.2; 435/252.3; 435/6; 435/320.1; 435/190; 435/468; 800/278; 800/295
(58) Field of Search ................. 435/190, 252.3, 435/320.1, 6, 440, 468; 536/23.2; 800/278, 295

(56) References Cited

PUBLICATIONS

Bartels et al., EMBO J., 10(5), 1037–1043, see the sequence alignment, May 1991.*
Li et al., Plant Mo. Biol., 29, 823–831, see the sequence alignment, Sep. 1995.*
Kuo et al., 1990, Plant Physiol., 93:1514–1520.
Loescher, 1987, Physiol. Plantarum, 70:553–557.
NCBI Identifier No. 113595, Aug. 1, 1992.
NCBI Identifier No. 2130022, Mar. 13, 1997.
NCBI Identifier No. 3378650, Aug. 1, 1998.
NCBI Identifier No. 1835701, Jun. 25, 1998.
NCBI Identifier No. 4519539, Mar. 9, 1999.
Embo, J., 10(5), 1037–1043, 1991.
Plant Mol. Biol., 29(4), 823–831, 1995.
Plant Physiol., 113(4), 1427–1435, 1997.
Plant Cell Physiol., 39(12), 1375–1379, 1998.

* cited by examiner

*Primary Examiner*—Rebecca E. Prouty
*Assistant Examiner*—M. Monshipouri

(57) ABSTRACT

This invention relates to an isolated nucleic acid fragment encoding a sorbitol biosynthetic enzyme. The invention also relates to the construction of a chimeric gene encoding all or a portion of the sorbitol biosynthetic enzyme, in sense or antisense orientation, wherein expression of the chimeric gene results in production of altered levels of the sorbitol biosynthetic enzyme in a transformed host cell.

10 Claims, No Drawings

PLANT SORBITOL BIOSYNTHETIC ENZYMES

This application claims the benefit of U.S. Provisional Application No. 60/092,952, filed Jul. 15, 1998.

FIELD OF THE INVENTION

This invention is in the field of plant molecular biology. More specifically, this invention pertains to nucleic acid fragments encoding sorbitol biosynthetic enzymes in plants and seeds.

BACKGROUND OF THE INVENTION

Sorbitol (D-glucitol) is an acyclic polyol found in a number of plant species (Kuo et al. (1990) *Plant Physiol* 93:1514–1520). Sorbitol is the primary photosynthetic product in rosaceous fruits and can account for a major portion of the carbon transported from the leaf. In corn sorbitol is found in seed and silk but not in pollen and leaf and low amounts of sorbitol are detectable in developing corn kernels. Sorbitol is found in soybeans and it is suggested that the accumulation of sorbitol may play a role in facilitating hexose metabolism in germinating seedlings (Kuo et al. (1990) *Plant Physiol* 93:1514–1520). During germination, soybeans convert oil and soluble oligosaccharides into sucrose which is in turn converted to glucose and fructose to fuel rapid growth. Some investigators have speculated that since plant fructokinases exhibit strong substrate inhibition by fructose, the presence of a sorbitol pathway may provide a mechanism to bypass this inhibition by converting excess fructose into sorbitol. This would help facilitate the metabolism of free glucose and fructose.

The metabolism of sorbitol has been extensively studied in several plant species (Kuo et al. (1990) *Plant Physiol* 93:1514–1520, Loescher (1987) *Physiol. Plantarum* 70:553–557, Loescher et al. in: Photoassimilate Distribution in Plants and Crops, ed. Zamski et al. Marcel Dekker, Inc., New York). There are several enzyme activities involved in sorbitol metabolism. Three of these enzymes are aldehyde reductase (NADPH-dependent aldose 6-phosphate reductase), sorbitol dehydrogenase, and NADP-dependent D-sorbitol-6-phosphate dehydrogenase. Aldehyde reductase appears responsible for the conversion of glucose to sorbitol; NADP-dependent D-sorbitol-6-phosphate dehydrogenase is also involved in sorbitol synthesis, and sorbitol dehydrogenase is involved in the conversion of sorbitol to fructose. Accordingly, the availability of nucleic acid sequences encoding all or a portion of these enzymes would facilitate studies to better understand carbohydrate metabolism and function in plants, provide genetic tools for the manipulation of the sorbitol biosynthetic pathway, and provide a means to control carbon partitioning in plant cells.

SUMMARY OF THE INVENTION

The instant invention relates to isolated nucleic acid fragments encoding sorbitol biosynthetic enzymes. Specifically, this invention concerns an isolated nucleic acid fragment encoding an aldehyde reductase, NADP-dependent D-sorbitol-6-phosphate dehydrogenase or sorbitol dehydrogenase and an isolated nucleic acid fragment that is substantially similar to an isolated nucleic acid fragment encoding a aldehyde reductase, NADP-dependent D-sorbitol-6-phosphate dehydrogenase or sorbitol dehydrogenase. In addition, this invention relates to a nucleic acid fragment that is complementary to the nucleic acid fragment encoding aldehyde reductase, NADP-dependent D-sorbitol-6-phosphate dehydrogenase or sorbitol dehydrogenase.

An additional embodiment of the instant invention pertains to a polypeptide encoding all or a substantial portion of a sorbitol biosynthetic enzyme selected from the group consisting of aldehyde reductase, NADP-dependent D-sorbitol-6-phosphate dehydrogenase or sorbitol dehydrogenase.

In another embodiment, the instant invention relates to a chimeric gene encoding an aldehyde reductase, NADP-dependent D-sorbitol-6-phosphate dehydrogenase or sorbitol dehydrogenase, or to a chimeric gene that comprises a nucleic acid fragment that is complementary to a nucleic acid fragment encoding an aldehyde reductase, NADP-dependent D-sorbitol-6-phosphate dehydrogenase or sorbitol dehydrogenase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an aldehyde reductase, NADP-dependent D-sorbitol-6-phosphate dehydrogenase or sorbitol dehydrogenase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an aldehyde reductase, NADP-dependent D-sorbitol-6-phosphate dehydrogenase or sorbitol dehydrogenase in a transformed host cell comprising: a) transforming a host cell with a chimeric gene comprising a nucleic acid fragment encoding an aldehyde reductase, NADP-dependent D-sorbitol-6-phosphate dehydrogenase or sorbitol dehydrogenase; and b) growing the transformed host cell under conditions that are suitable for expression of the chimeric gene wherein expression of the chimeric gene results in production of altered levels of aldehyde reductase, NADP-dependent D-sorbitol-6-phosphate dehydrogenase or sorbitol dehydrogenase in the transformed host cell.

An addition embodiment of the instant invention concerns a method for obtaining a nucleic acid fragment encoding all or a substantial portion of an amino acid sequence encoding an aldehyde reductase, NADP-dependent D-sorbitol-6-phosphate dehydrogenase or sorbitol dehydrogenase.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Sorbitol Biosynthetic Enzymes

| Protein | Clone Designation | SEQ ID NO: (Nucleotide) | (Amino Acid) |
|---|---|---|---|
| Aldehyde reductase | Contig composed of: | 1 | 2 |
|  | ccase-b.pk0023.g2 |  |  |
|  | ceb5.pk0015.g5 |  |  |
|  | ceb5.pk0032.e9 |  |  |
|  | ceb5.pk0044.c8 |  |  |
|  | ceb5.pk0049.d10 |  |  |
|  | ceb5.pk0052.a4 |  |  |
|  | ceb5.pk0052.h8 |  |  |
|  | ceb5.pk0062.a4 |  |  |
|  | ceb5.pk0075.e7 |  |  |
|  | ceb5.pk0075.g12 |  |  |
|  | cen6.pk0001.g2 |  |  |
| Aldehyde reductase | rca1n.pk022.j17 | 3 | 4 |
| Aldehyde reductase | sr1.pk0003.c5 | 5 | 6 |
| Aldehyde reductase | wl1n.pk0078.e5 | 7 | 8 |
| NADP-dependent D-sorbitol-6-phosphate dehydrogenase | p0002.cgevj66r | 9 | 10 |
| NADP-dependent D-sorbitol-6-phosphate dehydrogenase | rls2.pk0004.b8 | 11 | 12 |
| NADP-dependent D-sorbitol-6-phosphate dehydrogenase | ses2w.pk0038.e12 | 13 | 14 |
| Sorbitol dehydrogenase | p0113.cieae77r | 15 | 16 |
| Sorbitol dehydrogenase | rlr6.pk0096.b8 | 17 | 18 |
| Sorbitol dehydrogenase | sgs6c.pk001.122 | 19 | 20 |
| Sorbitol dehydrogenase | wlm96.pk0016.h12 | 21 | 22 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art.

Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several sorbitol biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other aldehyde reductase, NADP-dependent D-sorbitol-6-phosphate dehydrogenase or sorbitol dehydrogenase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the MRNA precursor encoding plant genes. Alternatively, the second primer sequence may be based upon sequences derived from the cloning vector. For example, the skilled artisan can follow the RACE protocol (Frohman et al. (1988) *Proc. Natl. Acad Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of sobitol biosynthesis in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sorbitol biosynthetic enzyme. An example of a vector for high level expression of the instant polypeptides in a bacterial host is provided (Example 8).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| ccase-b | Corn (Zea mays L.) type II callus tissue, somatic embryo formed | ccase-b.pk0023.g2 |
| ceb5 | Corn (Zea mays L.) amplified embryo 30 day | ceb5.pk0015.g5<br>ceb5.pk0032.e9<br>ceb5.pk0044.c8<br>ceb5.pk0049.d10<br>ceb5.pk0052.a4<br>ceb5.pk0052.h8<br>ceb5.pk0062.a4<br>ceb5.pk0075.e7<br>ceb5.pk0075.g12<br>cen6.pk0001.g2 |
| p0002 | Corn (Zea mays L.) tassel: premeiotic (> early uninucleate) | p0002.cgevj66r |
| p0113 | Corn (Zea mays L.) intercalary meristem of expanding internodes 5–9*; Sampled @ V10stage** | p0113.cieae77r |
| rca1n | Rice (Oryza sativa L.) callus* | rca1n.pk022.j17 |
| rlr6 | Rice (Oryza sativa L.) leaf (15 days after germination) 6 hrs after infection of Magaporthe grisea strain 4360-R-62 (AVR2-YAMO); Resistant | rlr6.pk0096.b8 |
| rls2 | Rice (Oryza sativa L.) leaf (15 DAG) 2 hrs after infection of Magaporthe grisea strain 4360-R-67 (avr2-yamo); Susceptible | rls2.pk0004.b8 |
| ses2w | Soybean (Glycine max L.) embryogenic suspension 2 weeks after subculture | ses2w.pk0038.e12 |
| sgs6c | Soybean (Glycine max L.) seeds 8 days after germination. | sgs6c.pk001.122 |
| sr1 | Soybean (Glycine max L.) root library | sr1.pk0003.c5 |
| wl1n | Wheat (Triticum aestivum L.) leaf 7 day old seedling, light grown* | wl1n.pk0078.e5 |
| wlm96 | Wheat (Triticum aestivum L.) seedlings 96 hr after inoculation w/E. graminis | wlm96.pk0016.h12 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif. The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651). The resulting ESTs are analyzed using a Perkin Elmer Model 377 fluorescent sequencer.

Example 2

Identification of cDNA Clones cDNA clones encoding sorbitol biosynthetic enzymes were identified by conducting BLAST (Basic Local Alignment Search Tool; Altschul et al. (1993) J. Mol. Biol. 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nature Genetics 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Aldehyde Reductase

The BLASTX search using the EST sequences from clones listed in Table 3 revealed similarity of the polypeptides encoded by the cDNAs to aldehyde reductase from Hordeum vulgare (NCBI Identifier No. gi 113595), Avena fatua (NCBI Identifier No. gi 2130022) and Medicago sativa (NCBI Identifier No. gi 3378650). Shown in Table 3 are the BLAST results for individual ESTs ("EST"), the sequences of the entire cDNA inserts comprising the indicated CDNA clones ("FIS"), or contigs assembled from two or more ESTs ("Contig"):

TABLE 3

BLAST Results for Sequences Encoding
Polypeptides Homologous to Hordeum vulgare,
Avena fatua and Medicago sativa Aldehyde Reductase

| Clone | Status | BLAST pLog Score |
|---|---|---|
| Contig composed of: | Contig | 171.00 (gi 113595) |
| ccase-b.pk0023.g2 | | |
| ceb5.pk0015.g5 | | |
| ceb5.pk0032.e9 | | |
| ceb5.pk0044.c8 | | |

TABLE 3-continued

BLAST Results for Sequences Encoding
Polypeptides Homologous to *Hordeum vulgare*,
*Avena fatua* and *Medicago sativa* Aldehyde Reductase

| Clone | Status | BLAST pLog Score |
|---|---|---|
| ceb5.pk0049.d10 | | |
| ceb5.pk0052.a4 | | |
| ceb5.pk0052.h8 | | |
| ceb5.pk0062.a4 | | |
| ceb5.pk0075.e7 | | |
| ceb5.pk0075.g12 | | |
| cen6.pk0001.g2 | | |
| rca1n.pk022.j17 | FIS | 172.00 (gi 2130022) |
| sr1.pk0003.c5 | FIS | 157.00 (gi 3378650) |
| wl1n.pk0078.e5 | EST | 112.00 (gi 3378650) |

The data in Table 4 represents a calculation of the percent identity of the amino acid sequences set forth in SEQ ID NOs:2, 4, 6 and 8 and the *Hordeum vulgare*, *Avena fatua* and *Medicago sativa* sequences (SEQ ID NOs:23, 24 and 25).

TABLE 4

Percent Identity of Amino Acid Sequences Deduced
From the Nucleotide Sequences of DNA Clones Encoding
Polypeptides Homologous to *Hordeum vulgare*, *Avena fatua*
and *Medicago sativa* Aldehyde Reductase

| SEQ ID NO. | Percent Identity to |
|---|---|
| 2 | 87% (gi 113595) |
| 4 | 90% (gi 2130022) |
| 6 | 84% (gi 3378650) |
| 8 | 61% (gi 3378650) |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an aldehyde reductase. These sequences represent the first corn, rice, soybean and wheat sequences encoding aldehyde reductase.

Example 4

Characterization of cDNA Clones Encoding NADPH-Dependent Mannose 6-Phosphate Dehydrogense The BLASTX search using the EST sequences from clones listed in Table 5 revealed similarity of the polypeptides encoded by the cDNAs to NADPH-dependent mannose 6-phosphate dehydrogense from *Apium graveolens* (NCBI Identifier No. gi 1835701). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding
Polypeptides Homologous to *Apium graveolens*
NADPH-Dependent Mannose 6-Phosphate Dehydrogense

| Clone | Status | BLAST pLog Score to (gi 1835701) |
|---|---|---|
| p0002.cgevj66r | EST | 134.00 |
| rls2.pk0004.b8 | FIS | 138.00 |
| ses2w.pk0038.e12 | EST | 138.00 |

The data in Table 6 represents a calculation of the percent identity of the amino acid sequences set forth in SEQ ID NOs: 10, 12 and 14 and the *Apium graveolens* sequences (SEQ ID NO:26).

TABLE 6

Percent Identity of Amino Acid Sequences Deduced
From the Nucleotide Sequences of DNA Clones Encoding
Polypeptides Homologous to *Apium graveolens*
NADPH-Dependent Mannose 6-Phosphate Dehydrogense

| SEQ ID NO. | Percent Identity to (gi 1835701) |
|---|---|
| 10 | 70% |
| 12 | 71% |
| 14 | 74% |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a NADPH-dependent mannose 6-phosphate dehydrogense. These sequences represent the first corn, rice and soybean sequences encoding NADPH-dependent mannose 6-phosphate dehydrogense.

Example 5

Characterization of cDNA Clones Encoding Sorbitol Dehydrogenase

The BLASTX search using the EST sequences from clones listed in Table 7 revealed similarity of the polypeptides encoded by the cDNAs to sorbitol dehydrogenase from *Malus domestica* (NCBI Identifier No. gi 4519539). Shown in Table 7 are the BLAST results for individual ESTs ("EST"), the sequences of the entire cDNA inserts comprising the indicated cDNA clones ("FIS"), or contigs assembled from two or more ESTs ("Contig"):

TABLE 7

BLAST Results for Sequences Encoding Polypeptides Homologous to *Malus domestica* Sorbitol Dehydrogenase

| Clone | Status | BLAST pLog Score to (gi 4519539) |
|---|---|---|
| p0113.cieae77r | EST | 158.00 |
| rlr6.pk0096.b8 | EST | 35.70 |
| sgs6c.pk001.122 | FIS | 133.00 |
| wlm96.pk0016.h12 | FIS | 129.00 |

The data in Table 8 represents a calculation of the percent identity of the amino acid sequences set forth in SEQ ID NOs:16, 18, 20 and 22 and the *Malus domestica* sequence (SEQ ID NO:27).

TABLE 8

Percent Identity of Amino Acid Sequences Deduced From the Nucleotide Sequences of DNA Clones Encoding Polypeptides Homologous to *Malus domestica* Sorbitol Dehydrogenase

| SEQ ID NO. | Percent Identity to (gi 4519539) |
|---|---|
| p0113.cieae77r | 71% |
| rlr6.pk0096.b8 | 45% |
| sgs6c.pk001.122 | 69% |
| wlm96.pk0016.h12 | 72% |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a sorbitol dehydrogenase. These sequences represent the first corn, rice, soybean and wheat sequences encoding sorbitol dehydrogenase.

Example 6

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 7

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having aldehyde reductase activity and comprising at least 300 amino acids, wherein, the amino acid sequence of the polypeptide and the amino acid sequence of SEQ ID NO:2, SEQ ID NO:4, SEQ ID NO:6, or SEQ ID NO:8 have at least 95% identity based on the Clustal alignment method, or
   (b) the complement of the nucleotide sequence.

2. The polynucleotide of claim 1 comprising the nucleotide sequence of SEQ ID NO: 1, SEQ ID NO:3, SEQ ID NO:5, or SEQ ID NO:7.

3. The polynucleotide of claim 1, wherein the polypeptide comprises the amino acid sequence of SEQ ID NO:2, SEQ ID NO:4, SEQ ID NO:6, or SEQ ID NO:8.

4. A chimeric gene comprising the polynucleotide of claim 1 operably linked to a regulatory sequence.

5. A vector comprising the polynucleotide of claim 1.

6. A cell comprising the chimeric gene of claim 4.

7. A method for transforming a cell comprising transforming a cell with the polynucleotide of claim 1.

8. A method for transforming a plant comprising transforming a plant cell with the polynucleotide of claim 1 and regenerating a plant from the transformed plant cell.

9. A plant comprising the chimeric gene of claim 4.

10. A seed comprising the chimeric gene of claim 4.

* * * * *

UNITED STATES PATENT AND TRADEMARK OFFICE
CERTIFICATE OF CORRECTION

PATENT NO.    : 6,274,379 B1
DATED         : August 14, 2001
INVENTOR(S)   : Famodu et al.

It is certified that error appears in the above-identified patent and that said Letters Patent is hereby corrected as shown below:

Column 7,
Line 6, "*Biochemistry ofPlants*" should be -- *Biochemistry of Plants* --.

Column 9,
Line 59, "sobitol" should be -- sorbitol --.

Column 11,
Line 1, "cosuppresion" should be -- cosuppression --.

Column 15,
Line 57, "Dehydrogense" should be -- Dehydrogenase --.
Line 62, "dehydrogense" should be -- dehydrogenase --.

Column 16,
Lines 5 and 24, "Dehydrogense" should be -- Dehydrogenase --.
Lines 46 and 49, "dehydrogense" should be -- dehydrogenase --.

Column 19,
Line 50, "embroys" should be -- embryos --.

Column 63,
Line 55, "aldhyde" should be -- aldehyde --.

Signed and Sealed this

First Day of July, 2003

JAMES E. ROGAN
*Director of the United States Patent and Trademark Office*

SEQUENCE LISTING

<160> NUMBER OF SEQ ID NOS: 27

<210> SEQ ID NO 1
<211> LENGTH: 1297
<212> TYPE: DNA
<213> ORGANISM: Zea mays

<400> SEQUENCE: 1

| | | | | | |
|---|---|---|---|---|---|
| ttttttcaa | gaagacagga | gaagggagtt | gtagtgagtt | ttaagaatgg | cgagtgcaca | 60 |
| ggcagtgggg | caaggagaac | gaggccactt | cgttctgaag | agcggacaca | ccattccggc | 120 |
| cgttggtcta | ggcacttgga | gggccggctc | agataccgct | cactctgttc | ggaccgccat | 180 |
| cgccgaggct | ggatataggc | acgtggacac | agctgcccaa | tacggagtag | agaaagaggt | 240 |
| cggtagagga | cttaaagctg | cgatggaggg | cgggatcaac | aggaaagatt | tgtttgtgac | 300 |
| gtcgaagcta | tggtgcaccg | agctggctcc | tgatagggtt | cggccagcac | tcgagaaaac | 360 |
| actcaaggac | ttgcagctgg | attacctgga | tctctacctt | atccactggc | ccttcaggct | 420 |
| gaaagacggg | gcgcacatgc | ccccggaagc | cggggaggtg | ctggagttcg | atatggaagg | 480 |
| ggtgtggagg | gagatggaag | gcctcgtgaa | agacgggctc | gtcaaggata | taggtgtctg | 540 |
| caattacacg | gtcgccaagc | tcaaccgcct | gatgcggtca | gcgaatgttc | caccggcagt | 600 |
| gtgccagatg | gaaatgcacc | ctgggtgaa | gaacgacagg | atctttgagg | catgcaagaa | 660 |
| gcatgggatc | catgttactg | cttactctcc | gctgggtccg | tcagagaaga | acctagcgca | 720 |
| cgacccgctc | gtcgaaaagg | tagccaacaa | actgacaag | accccgggc | aggtgctcct | 780 |
| caggtgggcg | ctccagaggg | ggacaagcgt | cattcctaaa | tcgaccaagg | acggaaggat | 840 |
| caaagagaac | atccaggtgt | tcgggtggga | gatccctgag | gaggacttca | gggccctgtg | 900 |
| cggcatcaaa | gatgagaagc | gcgtgctgac | cggagaggag | ctgttcgtga | acaagaccca | 960 |
| cgggccgtac | aagagcgcga | ccgaggtgtg | ggaccacgag | gactgagcgg | actgccgtgc | 1020 |
| cgccggatcc | ctccactcca | cctgatgaaa | ccagaataaa | ggataccgac | gcacctgtca | 1080 |
| gtcacctccc | tcccgtgcct | tgcgagagcg | gcagcctctc | gcacagggaa | gatgctctgt | 1140 |

```
gtctgagagc atgcagcctc gcacgagaaa gatgcagaag gagtgtgtgt ggcgcgcaat     1200
acactcctgt actgtacgat agactgaata ataataaaga agaaaacgca gcagtttgcc     1260
gttgcgtttt cctctgtgct tgcactatcg gtcgttc                              1297
```

<210> SEQ ID NO 2
<211> LENGTH: 319
<212> TYPE: PRT
<213> ORGANISM: Zea mays

<400> SEQUENCE: 2

```
Met Ala Ser Ala Gln Ala Val Gly Gln Gly Glu Arg Gly His Phe Val
  1               5                  10                  15

Leu Lys Ser Gly His Thr Ile Pro Ala Val Gly Leu Gly Thr Trp Arg
                 20                  25                  30

Ala Gly Ser Asp Thr Ala His Ser Val Arg Thr Ala Ile Ala Glu Ala
             35                  40                  45

Gly Tyr Arg His Val Asp Thr Ala Ala Gln Tyr Gly Val Glu Lys Glu
         50                  55                  60

Val Gly Arg Gly Leu Lys Ala Ala Met Glu Gly Gly Ile Asn Arg Lys
 65                  70                  75                  80

Asp Leu Phe Val Thr Ser Lys Leu Trp Cys Thr Glu Leu Ala Pro Asp
                 85                  90                  95

Arg Val Arg Pro Ala Leu Glu Lys Thr Leu Lys Asp Leu Gln Leu Asp
            100                 105                 110

Tyr Leu Asp Leu Tyr Leu Ile His Trp Pro Phe Arg Leu Lys Asp Gly
        115                 120                 125

Ala His Met Pro Pro Glu Ala Gly Glu Val Leu Glu Phe Asp Met Glu
    130                 135                 140

Gly Val Trp Arg Glu Met Glu Gly Leu Val Lys Asp Gly Leu Val Lys
145                 150                 155                 160

Asp Ile Gly Val Cys Asn Tyr Thr Val Ala Lys Leu Asn Arg Leu Met
                165                 170                 175

Arg Ser Ala Asn Val Pro Pro Ala Val Cys Gln Met Glu Met His Pro
            180                 185                 190

Gly Trp Lys Asn Asp Arg Ile Phe Glu Ala Cys Lys Lys His Gly Ile
        195                 200                 205

His Val Thr Ala Tyr Ser Pro Leu Gly Pro Ser Glu Lys Asn Leu Ala
    210                 215                 220

His Asp Pro Leu Val Glu Lys Val Ala Asn Lys Leu Asp Lys Thr Pro
225                 230                 235                 240

Gly Gln Val Leu Leu Arg Trp Ala Leu Gln Arg Gly Thr Ser Val Ile
                245                 250                 255

Pro Lys Ser Thr Lys Asp Gly Arg Ile Lys Glu Asn Ile Gln Val Phe
            260                 265                 270

Gly Trp Glu Ile Pro Glu Glu Asp Phe Arg Ala Leu Cys Gly Ile Lys
        275                 280                 285

Asp Glu Lys Arg Val Leu Thr Gly Glu Glu Leu Phe Val Asn Lys Thr
    290                 295                 300

His Gly Pro Tyr Lys Ser Ala Thr Glu Val Trp Asp His Glu Asp
305                 310                 315
```

<210> SEQ ID NO 3
<211> LENGTH: 1277
<212> TYPE: DNA

<213> ORGANISM: Oryza sativa

<400> SEQUENCE: 3

```
ggcacgagga aagtgaaga tagctaaacg gtgtgacaag caaggtaata gaaaggcgcg      60
atcatggcga gtgccaaggc gatggcgcag gatgagcatc actttgttct gaagagtggt    120
catgccatcc ctgcagttgg gttaggcact tggagggccg gctcagatac tgctcactcc    180
gttcagacag ccatcactga ggctggatac aggcatgtag atacggctgc tcaatatgga    240
atagaacagg aggtcggcaa agggcttaaa gctgcgatgg aagctggaat caacaggaaa    300
gatttgtttg tgacgtcaaa aatatggtgc acaaacttgg ctcctgagag agttcgacca    360
gcattaaaga acacgctgaa ggatctccag ttggattata tcgaccttta ccttattcat    420
tggcccttcc gtctaaaaga tggagcacac cagcctcctg aggctgggga agtcttggag    480
tttgacatgg aggcagtatg gagggaaatg gagagacttg tgacagatgg actggttaag    540
gacattggtg tctgcaattt ctcagttacc aagctcaaca gactgttgca atcagctaat    600
attccacctg cagtatgcca gatggaaatg caccctggtt ggaagaacaa taagattttc    660
gaggcctgca aaaacatgg aattcatgtt actgcctact ccccactggg ttcttctgaa    720
agaaccttg cgcatgatcc agttgtcgag aagatagcca acaagctgaa caagactcca    780
ggtcaagtgc tcatcaagtg ggctctccaa aggggaacaa gcgttattcc aaaatcaact    840
aaagatgaaa ggattaagga gaatatgcag gtgtttggat gggagatccc tgaagaggac    900
ttccaggtct tgtgcggcat caagatgag aagcgagtcc tgacaggaga ggagctcttc    960
gtgaacaaga cccatgggcc atacaagagt gcatctgagg tctgggataa cgaggactaa   1020
gctgccatgt ttcacccaaa gatatggcaa ataatggtta tgatgttggt catgcacgaa   1080
ggagttatgt gatgttctcc aagcactgtg acgaaaccag ctaactcagc acaagatgta   1140
ctactatgtg taaaactagt attgttctat gtgtgctctt cttcaagctt tgtgtaacca   1200
gcttctcagc acaagatgta cagccagtgc tgtaagataa ataaaagtat catggctttg   1260
ccgttgcact tgctact                                                    1277
```

<210> SEQ ID NO 4
<211> LENGTH: 318
<212> TYPE: PRT
<213> ORGANISM: Oryza sativa

<400> SEQUENCE: 4

```
Met Ala Ser Ala Lys Ala Met Ala Gln Asp Glu His His Phe Val Leu
  1               5                  10                  15

Lys Ser Gly His Ala Ile Pro Ala Val Gly Leu Gly Thr Trp Arg Ala
             20                  25                  30

Gly Ser Asp Thr Ala His Ser Val Gln Thr Ala Ile Thr Glu Ala Gly
         35                  40                  45

Tyr Arg His Val Asp Thr Ala Ala Gln Tyr Gly Ile Glu Gln Glu Val
     50                  55                  60

Gly Lys Gly Leu Lys Ala Ala Met Glu Ala Gly Ile Asn Arg Lys Asp
 65                  70                  75                  80

Leu Phe Val Thr Ser Lys Ile Trp Cys Thr Asn Leu Ala Pro Glu Arg
                 85                  90                  95

Val Arg Pro Ala Leu Lys Asn Thr Leu Lys Asp Leu Gln Leu Asp Tyr
            100                 105                 110

Ile Asp Leu Tyr Leu Ile His Trp Pro Phe Arg Leu Lys Asp Gly Ala
        115                 120                 125
```

```
His Gln Pro Pro Glu Ala Gly Glu Val Leu Phe Asp Met Glu Ala
    130                 135                 140

Val Trp Arg Glu Met Glu Arg Leu Val Thr Asp Gly Leu Val Lys Asp
145                 150                 155                 160

Ile Gly Val Cys Asn Phe Ser Val Thr Lys Leu Asn Arg Leu Leu Gln
                165                 170                 175

Ser Ala Asn Ile Pro Pro Ala Val Cys Gln Met Glu Met His Pro Gly
                180                 185                 190

Trp Lys Asn Asn Lys Ile Phe Glu Ala Cys Lys Lys His Gly Ile His
                195                 200                 205

Val Thr Ala Tyr Ser Pro Leu Gly Ser Ser Glu Lys Asn Leu Ala His
    210                 215                 220

Asp Pro Val Val Glu Lys Ile Ala Asn Lys Leu Asn Lys Thr Pro Gly
225                 230                 235                 240

Gln Val Leu Ile Lys Trp Ala Leu Gln Arg Gly Thr Ser Val Ile Pro
                245                 250                 255

Lys Ser Thr Lys Asp Glu Arg Ile Lys Glu Asn Met Gln Val Phe Gly
                260                 265                 270

Trp Glu Ile Pro Glu Glu Asp Phe Gln Val Leu Cys Gly Ile Lys Asp
                275                 280                 285

Glu Lys Arg Val Leu Thr Gly Glu Glu Leu Phe Val Asn Lys Thr His
    290                 295                 300

Gly Pro Tyr Lys Ser Ala Ser Glu Val Trp Asp Asn Glu Asp
305                 310                 315
```

<210> SEQ ID NO 5
<211> LENGTH: 1073
<212> TYPE: DNA
<213> ORGANISM: Glycine max

<400> SEQUENCE: 5

```
gcacgagcat ttctatttct aactaattat tgtgcttatt attattgttg agaaagaaaa      60
gaatggcaaa gttaataaaa ttctttgagt tgaacacagg ggccaagatt ccttctgttg     120
ggttaggcac ttggcaagct gagcctggtg ttgtagccaa agctgtcacc acagccattc     180
tggttggata caggcatatt gattgtgctc aagcgtataa caatcaagca gagattggtt     240
ctgctcttaa gaagcttttt gatgatggtg tggtgaagcg tgaggactta tggatcaccc     300
tccaaactct gtgttcagat catgcttcag aagatgtgcc caaagcattg gataaaacat     360
tgcaggattt gcaacttgat taccttgacc tctatctgat ccactggcca gtgcgcatga     420
aaagcggatc agttggattc aagaaggaat atctcgatca accggacatt cccagcacat     480
ggaaagcaat ggaggcactc tatgactcag gcaaggcaag agccatagga gttagcaatt     540
tctcttcaaa aaagcttcaa gatctcatga atatagcaag agtgcctcct gctgttaacc     600
aagtggaatt gcacccagga tgcagcagc caaagctgca tgcattctgt gaatctaaag      660
gagttcatct gtctggatat ctccactgg gctcaccagg agttctcaaa agtgacattc      720
ttaagaatcc tgttgtgata gagattgcag agaaattggg gaagacaccg gcacaagttg     780
cccttaggtg gggactgcaa acaggtcata gtgtgctgcc taagagcact aatgagtcca     840
gaatcaaggg aaactttgat gtgtttgact ggtctattcc agaagaagtg atggataagt     900
tctctgaaat taagcaggat agactaatta agggcacttt ttttgttgac gagacctatg     960
gtgcctttaa gaccgttgaa gagctttggg atggtgaact ctgagcaata tgcttcatag    1020
```
agatgttgac aaatgcactg ctcctcaagc agattgattc cgccttttac ctg         1073

<210> SEQ ID NO 6
<211> LENGTH: 313
<212> TYPE: PRT
<213> ORGANISM: Glycine max

<400> SEQUENCE: 6

```
Met Ala Lys Leu Ile Lys Phe Phe Glu Leu Asn Thr Gly Ala Lys Ile
 1               5                  10                  15

Pro Ser Val Gly Leu Gly Thr Trp Gln Ala Glu Pro Gly Val Val Ala
                20                  25                  30

Lys Ala Val Thr Thr Ala Ile Leu Val Gly Tyr Arg His Ile Asp Cys
            35                  40                  45

Ala Gln Ala Tyr Asn Asn Gln Ala Glu Ile Gly Ser Ala Leu Lys Lys
        50                  55                  60

Leu Phe Asp Asp Gly Val Val Lys Arg Glu Asp Leu Trp Ile Thr Ser
 65                  70                  75                  80

Lys Leu Trp Cys Ser Asp His Ala Ser Glu Asp Val Pro Lys Ala Leu
                85                  90                  95

Asp Lys Thr Leu Gln Asp Leu Gln Leu Asp Tyr Leu Asp Leu Tyr Leu
            100                 105                 110

Ile His Trp Pro Val Arg Met Lys Ser Gly Ser Val Gly Phe Lys Lys
        115                 120                 125

Glu Tyr Leu Asp Gln Pro Asp Ile Pro Ser Thr Trp Lys Ala Met Glu
    130                 135                 140

Ala Leu Tyr Asp Ser Gly Lys Ala Arg Ala Ile Gly Val Ser Asn Phe
145                 150                 155                 160

Ser Ser Lys Lys Leu Gln Asp Leu Met Asn Ile Ala Arg Val Pro Pro
                165                 170                 175

Ala Val Asn Gln Val Glu Leu His Pro Gly Trp Gln Gln Pro Lys Leu
            180                 185                 190

His Ala Phe Cys Glu Ser Lys Gly Val His Leu Ser Gly Tyr Ser Pro
        195                 200                 205

Leu Gly Ser Pro Gly Val Leu Lys Ser Asp Ile Leu Lys Asn Pro Val
    210                 215                 220

Val Ile Glu Ile Ala Glu Lys Leu Gly Lys Thr Pro Ala Gln Val Ala
225                 230                 235                 240

Leu Arg Trp Gly Leu Gln Thr Gly His Ser Val Leu Pro Lys Ser Thr
                245                 250                 255

Asn Glu Ser Arg Ile Lys Gly Asn Phe Asp Val Phe Asp Trp Ser Ile
            260                 265                 270

Pro Glu Glu Val Met Asp Lys Phe Ser Glu Ile Lys Gln Asp Arg Leu
        275                 280                 285

Ile Lys Gly Thr Phe Phe Val Asp Glu Thr Tyr Gly Ala Phe Lys Thr
    290                 295                 300

Val Glu Glu Leu Trp Asp Gly Glu Leu
305                 310
```

<210> SEQ ID NO 7
<211> LENGTH: 654
<212> TYPE: DNA
<213> ORGANISM: Triticum aestivum
<220> FEATURE:
<221> NAME/KEY: unsure
<222> LOCATION: (404)
<220> FEATURE:

-continued

```
<221> NAME/KEY: unsure
<222> LOCATION: (438)
<220> FEATURE:
<221> NAME/KEY: unsure
<222> LOCATION: (453)
<220> FEATURE:
<221> NAME/KEY: unsure
<222> LOCATION: (469)
<220> FEATURE:
<221> NAME/KEY: unsure
<222> LOCATION: (474)
<220> FEATURE:
<221> NAME/KEY: unsure
<222> LOCATION: (497)
<220> FEATURE:
<221> NAME/KEY: unsure
<222> LOCATION: (502)
<220> FEATURE:
<221> NAME/KEY: unsure
<222> LOCATION: (526)
<220> FEATURE:
<221> NAME/KEY: unsure
<222> LOCATION: (528)
<220> FEATURE:
<221> NAME/KEY: unsure
<222> LOCATION: (530)
<220> FEATURE:
<221> NAME/KEY: unsure
<222> LOCATION: (541)
<220> FEATURE:
<221> NAME/KEY: unsure
<222> LOCATION: (569)
<220> FEATURE:
<221> NAME/KEY: unsure
<222> LOCATION: (632)..(633)
<220> FEATURE:
<221> NAME/KEY: unsure
<222> LOCATION: (639)
<220> FEATURE:
<221> NAME/KEY: unsure
<222> LOCATION: (653)

<400> SEQUENCE: 7
attaaagatg gctgaatcct tgttctcag taccggctcg aggatcccat cggttgggct      60
tggcgtatgg caaatacaac ctgacgctgc aacgacgcc atctacgctg ctgtcaaggc     120
tgggtatcgg catattgact gtgcagcagc atacaacaat gaggaggagg tgggcctggc    180
tttgaagaaa ttatttgaag atggtgtggt taagcgtgat gatttgttta tcacctctaa    240
gctatgggct gctaatcatg cacctgaaga tgtggaagag ggaatcgaca ccacacttca    300
agatttgcag cttgactact tgggacttgt acctcatcca tggtccaatc cgcatcaaaa    360
aaaggaacta acacgatgac cctgaaaact tctccctaca gatncccctgc tacatgggca   420
gcgatggaga attatacnat ccggcaaaac tcntgcaatc cgcgtgatna ctcncttgta    480
agaactcatg attgctnccg tncacaatgc cccacatcaa caagtnantn caccggttgg    540
nacaagaaac tcggaacttc aatcaaggng tcacttcgat ccgcttagca ctgatcctga    600
taaggcattc taaaccatgg gccgtcaaaa tnnaaaacnc atcccacgga cang           654
```

<210> SEQ ID NO 8
<211> LENGTH: 308
<212> TYPE: PRT
<213> ORGANISM: Triticum aestivum

<400> SEQUENCE: 8

Phe Val Leu Ser Thr Gly Ser Arg Ile Pro Ser Val Gly Leu Gly Val
 1               5                  10                  15

Trp Gln Ile Gln Pro Asp Ala Ala Asn Asp Ala Ile Tyr Ala Ala Val
            20                  25                  30

```
Lys Ala Gly Tyr Arg His Ile Asp Cys Ala Ala Ala Tyr Asn Asn Glu
         35                  40                  45
Glu Glu Val Gly Leu Ala Leu Lys Lys Leu Phe Glu Asp Gly Val Val
 50                  55                  60
Lys Arg Asp Asp Leu Phe Ile Thr Ser Lys Leu Trp Ala Ala Asn His
 65                  70                  75                  80
Ala Pro Glu Asp Val Glu Gly Ile Asp Thr Thr Leu Gln Asp Leu
                 85                  90                  95
Gln Leu Asp Tyr Leu Asp Leu Tyr Leu Ile His Gly Pro Ile Arg Ile
                100                 105                 110
Lys Lys Gly Thr Ser Thr Met Thr Pro Glu Asn Phe Leu Pro Thr Asp
                115                 120                 125
Ile Pro Ala Thr Trp Ala Ala Met Glu Lys Leu Tyr Asp Ser Gly Lys
130                 135                 140
Ala Arg Ala Ile Gly Val Ser Asn Phe Ser Cys Lys Lys Leu His Asp
145                 150                 155                 160
Leu Leu Ala Val Ala Arg Val Pro Pro Ala Val Asn Gln Val Glu Cys
                165                 170                 175
His Pro Val Trp Gln Gln Asp Lys Leu Arg Lys Leu Cys Gln Ser Asn
                180                 185                 190
Gly Val His Leu Ser Ala Phe Ser Pro Leu Gly Ser Pro Gly Ser Pro
                195                 200                 205
Trp Ile Asn Gly Pro Ser Val Leu Lys Asn Pro Ile Val Val Ser Val
                210                 215                 220
Ala Asp Lys Leu Gln Lys Thr Pro Ala Gln Val Ala Leu Arg Trp Gly
225                 230                 235                 240
Ile Gln Met Gly His Ser Val Leu Pro Lys Ser Ala Asn Glu Ser Arg
                245                 250                 255
Ile Lys Glu Asn Ile Asp Ile Phe Gly Trp Ser Ile Pro Glu Asp Leu
                260                 265                 270
Met Ala Lys Phe Ser Glu Ile Lys Gln Val Arg Leu Leu Thr Ala Glu
                275                 280                 285
Phe Val Val His Pro Gln Ala Gly Tyr Asn Thr Leu Glu Asp Phe Trp
                290                 295                 300
Asp Gly Glu Ile
305
```

```
<210> SEQ ID NO 9
<211> LENGTH: 406
<212> TYPE: DNA
<213> ORGANISM: Zea mays
<220> FEATURE:
<221> NAME/KEY: unsure
<222> LOCATION: (76)
<220> FEATURE:
<221> NAME/KEY: unsure
<222> LOCATION: (320)
<220> FEATURE:
<221> NAME/KEY: unsure
<222> LOCATION: (406)

<400> SEQUENCE: 9
tgccaacgag gcgaacagcc ggccaatcta gcatcagcgc gcggggtctg agagcagagc      60
ggcagggcgc catggnggca tcggtggcgc tgagcagcgg gcaccggatg ccggcggtgg     120
ggctgggcgt gtggcggatg gagaaggcgg acatccgcgg cctcatccac acagcgctcc     180
gcgtcggcta ccgccacctg gactgcgccg ctgactacca gaacgaagct gaagttggtg     240
```

```
acgcgctcgc agaggcattc cagaccggac tcgtcaagcg ggaggacctg ttcatcacaa    300
ccaagctgtg gaactcagan catgggcatg tgcttgaagc ctgcaaggac agcctgaaga    360
agctgcagct agactatctc gacctctacc tcatccattt cccagn                   406
```

<210> SEQ ID NO 10
<211> LENGTH: 308
<212> TYPE: PRT
<213> ORGANISM: Zea mays

<400> SEQUENCE: 10

```
Ser Val Ala Leu Ser Gly His Arg Met Pro Ala Val Gly Leu Gly
  1               5                  10                  15

Val Trp Arg Met Glu Lys Ala Asp Ile Arg Gly Leu Ile His Thr Ala
                 20                  25                  30

Leu Arg Val Gly Tyr Arg His Leu Asp Cys Ala Ala Asp Tyr Gln Asn
             35                  40                  45

Glu Ala Glu Val Gly Asp Ala Leu Ala Glu Ala Phe Gln Thr Gly Leu
         50                  55                  60

Val Lys Arg Glu Asp Leu Phe Ile Thr Thr Lys Leu Trp Asn Ser Asp
 65                  70                  75                  80

His Gly His Val Leu Glu Ala Cys Lys Asp Ser Leu Lys Lys Leu Gln
                 85                  90                  95

Leu Asp Tyr Leu Asp Leu Tyr Leu Ile His Phe Pro Val Ala Thr Arg
            100                 105                 110

His Thr Gly Val Gly Thr Thr Ser Ala Leu Gly Asp Asp Gly Val
        115                 120                 125

Leu Asp Ile Asp Thr Thr Ile Ser Leu Glu Thr Thr Trp His Ala Met
130                 135                 140

Glu Glu Leu Val Ser Met Gly Leu Val Arg Ser Ile Gly Ile Ser Asn
145                 150                 155                 160

Tyr Asp Ile Phe Leu Thr Arg Asp Cys Leu Ala Tyr Ala Lys Ile Lys
                165                 170                 175

Pro Ala Val Asn Gln Ile Glu Thr His Pro Tyr Phe Gln Arg Asp Ser
            180                 185                 190

Leu Val Lys Phe Cys Gln Lys His Gly Ile Cys Val Thr Ala His Thr
        195                 200                 205

Pro Leu Gly Gly Ser Thr Ala Asn Ala Glu Trp Phe Gly Thr Val Ser
    210                 215                 220

Cys Leu Asp Asp Pro Val Ile Lys Ser Leu Ala Asp Lys Tyr Gly Lys
225                 230                 235                 240

Thr Pro Ala Gln Leu Val Leu Arg Trp Gly Leu Gln Arg Asp Thr Val
                245                 250                 255

Val Ile Pro Lys Thr Ser Lys Val Glu Arg Leu Gln Glu Asn Phe Asp
            260                 265                 270

Val Phe Gly Phe Asp Ile Ser Gly Glu Asp Met Glu Arg Met Lys Ala
        275                 280                 285

Ile Asp Arg Lys Tyr Arg Thr Asn Gln Pro Ala Lys Phe Trp Gly Ile
    290                 295                 300

Asp Leu Tyr Ala
305
```

<210> SEQ ID NO 11
<211> LENGTH: 1683
<212> TYPE: DNA

<213> ORGANISM: Oryza sativa

<400> SEQUENCE: 11

```
gcacgagctt cttcttctcg tctccgattc caacgaggcg gcggagcaga gcagaggcgc      60
gggatggcgg cggcgcaggg gagcggagtg ccggcggcgc tggcgctgag cagcggccac     120
acgatgccgt cggtggggtt gggcgtgtgg cggatggact cccccgccat ccgcgacctc     180
atccactccg cactccgcat cggctaccgc cacttcgact gcgccgctga ttaccaaaac     240
gaggctgaag ttggggatgc acttgcagag gcattccaaa ctggacttgt caagagggag     300
gatcttttca tcacaaccaa gttgtggaac tcagatcatg gcatgtggt tgaagcatgt      360
aaggatagct tgaaaaagtt gcggctagat tatctagatc tctaccttat ccacttccca     420
gtagctaccc gtcatactgg agttggtacg actgctagtg ctcttggtga tgatggtgtg     480
ctagacattg ataccactat ctcattggag acaacatggc acgctatgga ggatcttgtt     540
tccatgggac tggttcgcag cattgggatt agcaactatg acatattcct taccagagat     600
tgtttggctt atgctaagat aaagcccgca gtgaatcaaa tcgagacaca tccctacttc     660
cagcgcgact gtcttgtcaa gttctgccag aagcatggga tcttagtcac tgcccatacc     720
cctctgggtg gctccactgc caatactgag tggtttgggt ccgtctcatg cctcgacgac     780
cctgtcatca agtctctggc tgagaaatat ggcaagacac cggcgcagct ggtgctccgg     840
tgggggcttc agaggaacac agtggtgatc cccaagacat ccaaggagga gagattgcag     900
gagaactttg cggtcttcga tttcgccatc tccgacgagg acatggagaa gatgagatcc     960
atcgaccgga gtaccgcac caaccagcct gccaagttct ggggaatcga cctgtttgct    1020
tgatgaatta tgagtcttta gcacgaacaa taatgggggc ttttctactg tccctgggag    1080
cttcttgtgc aatcattttt ctctgaactg aaacttcttg tgctgaagga tgaagttgtt    1140
gggatcgtgt gaacttgaat tgttattcaa agggaaaaaa aaagtgtgaa cttgaattgt    1200
atctatattt cgtgtatttg cgcttctgca aaaaaaaaa aaaaaaaaaa aaaaaaaaa      1260
aaaaaaaaaa aaaaaaaaca aacaaaaaaa aaaaaaaaaa aaaaaaaaaa aaaaaaaac     1320
cccccggggg ggggccggga accaattccc cccaaaaggg ggccgtttaa ccccccccaa     1380
ggggcggtct tttaaaaact ccgggagggg aaaaacccgg ggtttaccaa attaaccccc     1440
ttgggaaaaa acccccttttt cccaaatggg gtaaaaacca aagggccccc caccattccc     1500
cttcccaaaa atttgccaac cctaaaggga aatgggaacc ccccttgtac gggcaaataa     1560
accccgcgg gtttggggtt tccccacac gggcccgtaa aacttgaaag cccctaagcg     1620
ccggccccctt tgcgttttttt ccccctcctt ttccccacaa gtttgcccgg gtttcccga     1680
cag                                                                 1683
```

<210> SEQ ID NO 12
<211> LENGTH: 308
<212> TYPE: PRT
<213> ORGANISM: Oryza sativa

<400> SEQUENCE: 12

```
Ala Leu Ala Leu Ser Ser Gly His Thr Met Pro Ser Val Gly Leu Gly
 1               5                  10                  15

Val Trp Arg Met Asp Ser Pro Ala Ile Arg Asp Leu Ile His Ser Ala
            20                  25                  30

Leu Arg Ile Gly Tyr Arg His Phe Asp Cys Ala Ala Asp Tyr Gln Asn
        35                  40                  45
```

```
Glu Ala Glu Val Gly Asp Ala Leu Ala Glu Ala Phe Gln Thr Gly Leu
     50                  55                  60

Val Lys Arg Glu Asp Leu Phe Ile Thr Thr Lys Leu Trp Asn Ser Asp
 65                  70                  75                  80

His Gly His Val Val Glu Ala Cys Lys Asp Ser Leu Lys Lys Leu Arg
                 85                  90                  95

Leu Asp Tyr Leu Asp Leu Tyr Leu Ile His Phe Pro Val Ala Thr Arg
                100                 105                 110

His Thr Gly Val Gly Thr Thr Ala Ser Ala Leu Gly Asp Asp Gly Val
                115                 120                 125

Leu Asp Ile Asp Thr Thr Ile Ser Leu Glu Thr Thr Trp His Ala Met
            130                 135                 140

Glu Asp Leu Val Ser Met Gly Leu Val Arg Ser Ile Gly Ile Ser Asn
145                 150                 155                 160

Tyr Asp Ile Phe Leu Thr Arg Asp Cys Leu Ala Tyr Ala Lys Ile Lys
                165                 170                 175

Pro Ala Val Asn Gln Ile Glu Thr His Pro Tyr Phe Gln Arg Asp Cys
                180                 185                 190

Leu Val Lys Phe Cys Gln Lys His Gly Ile Leu Val Thr Ala His Thr
            195                 200                 205

Pro Leu Gly Gly Ser Thr Ala Asn Thr Glu Trp Phe Gly Ser Val Ser
    210                 215                 220

Cys Leu Asp Asp Pro Val Ile Lys Ser Leu Ala Glu Lys Tyr Gly Lys
225                 230                 235                 240

Thr Pro Ala Gln Leu Val Leu Arg Trp Gly Leu Gln Arg Asn Thr Val
                245                 250                 255

Val Ile Pro Lys Thr Ser Lys Glu Glu Arg Leu Gln Glu Asn Phe Ala
                260                 265                 270

Val Phe Asp Phe Ala Ile Ser Asp Glu Asp Met Glu Lys Met Arg Ser
            275                 280                 285

Ile Asp Arg Lys Tyr Arg Thr Asn Gln Pro Ala Lys Phe Trp Gly Ile
    290                 295                 300

Asp Leu Phe Ala
305
```

<210> SEQ ID NO 13
<211> LENGTH: 560
<212> TYPE: DNA
<213> ORGANISM: Glycine max
<220> FEATURE:
<221> NAME/KEY: unsure
<222> LOCATION: (106)
<220> FEATURE:
<221> NAME/KEY: unsure
<222> LOCATION: (461)
<220> FEATURE:
<221> NAME/KEY: unsure
<222> LOCATION: (495)
<220> FEATURE:
<221> NAME/KEY: unsure
<222> LOCATION: (551)

<400> SEQUENCE: 13
ggaagagaga aaaccatgg caataacact caacaatggc ttcaagatgc ctatcattgg     60
attgggcgtg tggcgcatgg aaggaaacga atcagggac ctaatntctc aattccatca    120
aaattggtta tcgccatttt gattgtgctg ctgactacaa aaacgaagca gaagttggag   180
atgcgcttaa ggaggctttt gatagtggcc ttgtgaagag agaggatctc ttcattacca   240

```
ccaagctttg gaattctgat caaggccacg ttcttgaggc gtgtaaagac agtctcaaga      300
agcttcagtt aacgtatcta gatttatatc ttgttcactt tcctgttgcc gtaaggatac      360
tggggttggt aatacttcta gtcctttggg tgatgatggg gcctggacat agtacaccat      420
tccctggaaa cgacctggca tgcaatggaa gatcttgttt ntcggcttgt tcgcagcata      480
ggtcgcacta tgtanttctg acagagatgt tacatattca gtaagctgc tgtaatcgat        540 gaactcatca ncttcaggtg                                                   560
```

<210> SEQ ID NO 14
<211> LENGTH: 309
<212> TYPE: PRT
<213> ORGANISM: Glycine max

<400> SEQUENCE: 14

```
Met Ala Ile Thr Leu Asn Asn Gly Phe Lys Met Pro Ile Ile Gly Leu
 1               5                  10                  15

Gly Val Trp Arg Met Glu Gly Asn Glu Ile Arg Asp Leu Ile Leu Asn
            20                  25                  30

Ser Ile Lys Ile Gly Tyr Arg His Phe Asp Cys Ala Ala Asp Tyr Lys
        35                  40                  45

Asn Glu Ala Glu Val Gly Asp Ala Leu Lys Glu Ala Phe Asp Ser Gly
    50                  55                  60

Leu Val Lys Arg Glu Asp Leu Phe Ile Thr Thr Lys Leu Trp Asn Ser
65                  70                  75                  80

Asp Gln Gly His Val Leu Glu Ala Cys Lys Asp Ser Leu Lys Lys Leu
                85                  90                  95

Gln Leu Thr Tyr Leu Asp Leu Tyr Leu Val His Phe Pro Val Ala Val
            100                 105                 110

Arg His Thr Gly Val Gly Asn Thr Ser Ser Pro Leu Gly Asp Asp Gly
        115                 120                 125

Val Leu Asp Ile Asp Thr Thr Ile Ser Leu Glu Thr Thr Trp His Ala
    130                 135                 140

Met Glu Asp Leu Val Ser Ser Gly Leu Val Arg Ser Ile Gly Ile Ser
145                 150                 155                 160

Asn Tyr Asp Ile Phe Leu Thr Arg Asp Cys Leu Ala Tyr Ser Lys Ile
                165                 170                 175

Lys Pro Ala Val Asn Gln Ile Glu Thr His Pro Tyr Phe Gln Arg Asp
            180                 185                 190

Ser Leu Val Lys Phe Cys Gln Lys His Gly Ile Cys Val Thr Ala His
        195                 200                 205

Thr Pro Leu Gly Gly Ala Ala Asn Ala Glu Trp Phe Gly Thr Val
    210                 215                 220

Ser Cys Leu Asp Asp Gln Val Leu Lys Gly Leu Ala Glu Lys Tyr Lys
225                 230                 235                 240

Lys Thr Ala Ala Gln Ile Ser Leu Arg Trp Gly Ile Gln Arg Asn Thr
                245                 250                 255

Val Val Ile Pro Lys Ser Ser Lys Leu Glu Arg Leu Lys Glu Asn Phe
            260                 265                 270

Gln Val Phe Asp Phe Glu Leu Ser Lys Glu Asp Met Glu Leu Ile Gly
        275                 280                 285

Ser Ile Asp Arg Lys Tyr Arg Thr Asn Gln Pro Ala Val Phe Trp Gly
    290                 295                 300

Ile Asp Leu Tyr Ala
305
```

<210> SEQ ID NO 15
<211> LENGTH: 1154
<212> TYPE: DNA
<213> ORGANISM: Zea mays

<400> SEQUENCE: 15

```
ccacgcgtcc gctcatctgc gtacacggtc tccctcttcc tgtcagtagt agagtgagag    60
tgaggcagcg agtgggagac aagggggaaat gggaagggga gcgcaaggga gcgatgcggc   120
ggcggcgggc ggcgaggtgg aggagaacat ggcggcgtgg ctggttgcca agaacaccct   180
caagatcatg cccttcaagc tcccgcccgt cggcccttat gatgtccgcg tgcgcatgaa   240
agcagtgggg atttgcggca gcgatgtgca ctacctcagg gagatgcgca tcgcgcactt   300
cgtggtgaag gagccgatgg tgatcgggca cgagtgcgcg ggcgtggtcg aggaggtggg   360
cgccggcgtg acgcacctgt ccgtgggcga ccgcgtggcc ctggagccgg cgtcagctg    420
ctggcgctgc cgccactgca agggcgggcg gtacaaccct gtgcgaggaa catgaagttc   480
ttcgccaccc cgccggtgca cggctcgctg gcgaaccagg tggtgcaccc ggccgacctg   540
tgcttcaagc tccccgacgg ggtgagcctg aggagggcg ccatgtgcga gccgctgagc   600
gtgggcgtgc acgcgtgccg ccgcgcgggg gtggggcccg agacgggcgt gctcgtggtg   660
ggcgccggcc ccatcggcct ggtgtcgctg ctagcggcgc gagccttcgg cgcgccgcgc   720
gtggtggtcg tggacgtgga cgaccaccgc ctggccgtgg cccaggtcgc tgggcgcgga   780
cgcggcggtg cgggtgtcgc cccgcgcgga ggacctggcg gacgaggtgg agcgcatccg   840
cgcggccatg ggctcggaca tcgacgtcag cctggactgc gccgggttca gcaagaccat   900
gtcgacggcg ctggaggcga cgcggcccgg cgggaaggtg tgcctggtcg ggatgggcca   960
caacgagatg acgctgcccc tgacggcggc ggcggcgcgg gaggtggacg tggtgggcgt  1020
gttccggtac aaggacacct ggccgctgtg catcgacttc ctgcgcagcg gcaaggtgga  1080
cgtcaagccg ctcatcaccc accgcttcgg tttctcgcag cgggacgtgg aggaggcctt  1140
cgaggtcagc gccc                                                    1154
```

<210> SEQ ID NO 16
<211> LENGTH: 341
<212> TYPE: PRT
<213> ORGANISM: Zea mays

<400> SEQUENCE: 16

```
Ala Ala Ala Gly Gly Glu Val Glu Glu Asn Met Ala Ala Trp Leu Val
 1               5                  10                  15

Ala Lys Asn Thr Leu Lys Ile Met Pro Phe Lys Leu Pro Pro Val Gly
                20                  25                  30

Pro Tyr Asp Val Arg Val Arg Met Lys Ala Val Gly Ile Cys Gly Ser
            35                  40                  45

Asp Val His Tyr Leu Arg Glu Met Arg Ile Ala His Phe Val Lys
        50                  55                  60

Glu Pro Met Val Ile Gly His Glu Cys Ala Gly Val Val Glu Glu Val
 65                  70                  75                  80

Gly Ala Gly Val Thr His Leu Ser Val Gly Asp Arg Val Ala Leu Glu
                85                  90                  95

Pro Gly Val Ser Cys Trp Arg Cys Arg His Cys Lys Gly Gly Arg Tyr
            100                 105                 110

Asn Pro Val Arg Asn Met Lys Phe Phe Ala Thr Pro Pro Val His Gly
```

```
                115                 120                 125
Ser Leu Ala Asn Gln Val Val His Pro Ala Asp Leu Cys Phe Lys Leu
    130                 135                 140

Pro Asp Gly Val Ser Leu Glu Glu Gly Ala Met Cys Glu Pro Leu Ser
145                 150                 155                 160

Val Gly Val His Ala Cys Arg Arg Ala Gly Val Gly Pro Glu Thr Gly
                165                 170                 175

Val Leu Val Val Gly Ala Gly Pro Ile Gly Leu Val Ser Leu Leu Ala
            180                 185                 190

Ala Arg Ala Phe Gly Ala Pro Arg Val Val Val Asp Val Asp Asp
        195                 200                 205

His Arg Leu Ala Val Ala Arg Ser Leu Gly Ala Asp Ala Ala Val Arg
    210                 215                 220

Val Ser Pro Arg Ala Glu Asp Leu Ala Asp Glu Val Glu Arg Ile Arg
225                 230                 235                 240

Ala Ala Met Gly Ser Asp Ile Asp Val Ser Leu Asp Cys Ala Gly Phe
                245                 250                 255

Ser Lys Thr Met Ser Thr Ala Leu Glu Ala Thr Arg Pro Gly Gly Lys
            260                 265                 270

Val Cys Leu Val Gly Met Gly His Asn Glu Met Thr Leu Pro Leu Ala
        275                 280                 285

Ala Arg Glu Val Asp Val Val Gly Val Phe Arg Tyr Lys Asp Thr Trp
    290                 295                 300

Pro Leu Cys Ile Asp Phe Leu Arg Ser Gly Lys Val Asp Val Lys Pro
305                 310                 315                 320

Leu Ile Thr His Arg Phe Gly Phe Ser Gln Arg Asp Val Glu Glu Ala
                325                 330                 335

Phe Glu Val Ser Ala
            340

<210> SEQ ID NO 17
<211> LENGTH: 718
<212> TYPE: DNA
<213> ORGANISM: Oryza sativa
<220> FEATURE:
<221> NAME/KEY: unsure
<222> LOCATION: (313)..(314)
<220> FEATURE:
<221> NAME/KEY: unsure
<222> LOCATION: (351)
<220> FEATURE:
<221> NAME/KEY: unsure
<222> LOCATION: (418)
<220> FEATURE:
<221> NAME/KEY: unsure
<222> LOCATION: (470)
<220> FEATURE:
<221> NAME/KEY: unsure
<222> LOCATION: (514)
<220> FEATURE:
<221> NAME/KEY: unsure
<222> LOCATION: (519)
<220> FEATURE:
<221> NAME/KEY: unsure
<222> LOCATION: (524)
<220> FEATURE:
<221> NAME/KEY: unsure
<222> LOCATION: (527)
<220> FEATURE:
<221> NAME/KEY: unsure
<222> LOCATION: (537)
<220> FEATURE:
<221> NAME/KEY: unsure
<222> LOCATION: (548)
```

```
<220> FEATURE:
<221> NAME/KEY: unsure
<222> LOCATION: (618)
<220> FEATURE:
<221> NAME/KEY: unsure
<222> LOCATION: (631)
<220> FEATURE:
<221> NAME/KEY: unsure
<222> LOCATION: (635)
<220> FEATURE:
<221> NAME/KEY: unsure
<222> LOCATION: (646)
<220> FEATURE:
<221> NAME/KEY: unsure
<222> LOCATION: (680)
<220> FEATURE:
<221> NAME/KEY: unsure
<222> LOCATION: (691)
<220> FEATURE:
<221> NAME/KEY: unsure
<222> LOCATION: (693)
<220> FEATURE:
<221> NAME/KEY: unsure
<222> LOCATION: (702)
<220> FEATURE:
<221> NAME/KEY: unsure
<222> LOCATION: (706)
<220> FEATURE:
<221> NAME/KEY: unsure
<222> LOCATION: (717)..(718)

<400> SEQUENCE: 17
gtttaaacga gtgagtgagt gaagaggagg aagatgggga agggagggaa aggagccgag      60
gcggcggcgg cggcggtggc cggagccggt gaggaggaga acatggcggc gtggctggtg     120
gcgaagaaca ccctcaagat catgcccttc aagctcccgc cagttgggcc ttatgatgtc     180
cgtgtccgga tgaaggcagt gggcatctgc ggcagcgacg tgcactacct cagggagatg     240
cgcattgcgc atttcgtggt gaaggagccg atggtgatcg gcacgagtg cgccggcgtg      300 atagaggagg tcnngcagcg gcgtgaccac ctcgccgtcg gcgaccgcgt nggcgctcga     360
gcccggcatc aactgctggc gctcaagcac tgcaagggcg ccgctacaa cttctgcnaa      420 gacatgaatt cttcgccacc ctcccgttca cggttcctcg ccaacaaatn gtcacctgtg     480
atctgtgctc aagctccgga gaacttaacc tgangaagng catntcnaac cctgacntgg     540
cttcaccntg cgcgcccact ccggcggaaa cggggtctat tatggccggg ccatttgctg     600
tcacctctgc gcccccctngg caacctctat ntgcntgcaa accctnctgc attctggcca     660
ccctagttcg ccccagattn caggtgacgt ngngatggga tntacntccg taaaagnn       718

<210> SEQ ID NO 18
<211> LENGTH: 159
<212> TYPE: PRT
<213> ORGANISM: Oryza sativa
<220> FEATURE:
<221> NAME/KEY: UNSURE
<222> LOCATION: (94)
<220> FEATURE:
<221> NAME/KEY: UNSURE
<222> LOCATION: (129)
<220> FEATURE:
<221> NAME/KEY: UNSURE
<222> LOCATION: (146)

<400> SEQUENCE: 18

Met Gly Lys Gly Gly Lys Gly Ala Glu Ala Ala Ala Ala Val Ala
 1               5                  10                  15

Gly Ala Gly Glu Glu Glu Asn Met Ala Ala Trp Leu Val Ala Lys Asn
                20                  25                  30
```

```
Thr Leu Lys Ile Met Pro Phe Lys Leu Pro Pro Val Gly Pro Tyr Asp
         35                  40                  45

Val Arg Val Arg Met Lys Ala Val Gly Ile Cys Gly Ser Asp Val His
 50                  55                  60

Tyr Leu Arg Glu Met Arg Ile Ala His Phe Val Val Lys Glu Pro Met
 65                  70                  75                  80

Val Ile Gly His Glu Cys Ala Gly Val Ile Glu Val Xaa Gln Arg
                 85                  90                  95

Arg Asp His Leu Ala Val Gly Asp Arg Val Gly Ala Arg Ala Arg His
            100                 105                 110

Gln Leu Leu Ala Leu Lys His Cys Lys Gly Gly Arg Tyr Asn Phe Cys
        115                 120                 125

Xaa Asp Met Asn Ser Ser Pro Pro Ser Arg Ser Arg Phe Leu Ala Asn
130                 135                 140

Lys Xaa Ser Pro Val Ile Cys Ala Gln Ala Pro Glu Asn Leu Thr
145                 150                 155
```

<210> SEQ ID NO 19
<211> LENGTH: 1610
<212> TYPE: DNA
<213> ORGANISM: Glycine max

<400> SEQUENCE: 19

```
ttcggcacga ggaaatgggt aaggggggaa tgtcaattga tgaacatgga gaaggcaaag      60
aagagaatat ggctgcttgg cttgttggaa tgaacactct caagattcag cctttcaagc     120
ttcctacttt gggacccgat gatgtcgag ttagaatgaa ggctgttggt atctgtggga     180
gtgatgttca ctacctcaag acactgaggt gtgctcactt tatagttaaa gaaccaatgg     240
ttattggtca tgagtgtgct gggatcatag aagaagttgg tagtcaggta aagagtttgg     300
tgcctggtga ccgtgtggca attgagcctg ggatcagttg ttggcattgc aaccattgca     360
aacacggtcg atataactta tgcgatgata tgaagttttt tgctactcca ccagttcatg     420
gttccctggc taatcagata gtgcatcctg cagacctatg ttttaagctg ccagacaacg     480
tgagcctaga ggagggagca atgtgtgaac ccttaagtgt tggtgttcat gcttgtagaa     540
gagctaatat tggaccagaa acaaatgtgt tgatcatggg agcagggccc ataggacttg     600
ttacaatgct ggcagctcgt gcgtttgggg cacccaaaac agtcattgtg atgttgatg      660
accatcgttt atctgttgca aaatctcttg gtgcagatga tattattaaa gtctcaacaa     720
acattaagga tgtggctgaa gaagttgtgc agatacagaa ggttatggga gctggtatag     780
atgttacctt tgattgtgct ggttttgaca aaaccatgtc tccagcactg agtgctactc     840
agccaggtgg caaagtttgc ctagtgggaa tgggacattc tgaaatgact gtcccactca     900
cccccagctg cagcaagttg tattggattt tcatcacatt tttaaaggct tggatacttc     960
actgatacat accgctgata tatccaagga agttgatgtg gttggagttt tcgctatat     1020
gaacacatgg cctctttgcc ttgagtttct aaggagtggc aaaattgatg tgaaacccct    1080
tataacgcac aggtttggat tctctcaaaa ggaagtggaa gaagcctttg aaacaactgc    1140
tcgtggtggt aacgccatca aggtcatgtt caatctttag atactggact gtgactttac    1200
aaactgtcgt atgttgaaca agtaggtaa tttacatgtt catgctcatg ttaaatacca    1260
atgtattgat aacacgggtt atgaataaag tggtttcaag aaggacttgt aaaacatgtt    1320
aatggtaact gcagcatcta cagattcagt tatgaagtga aactttttct taatatgtta   1380
```

```
atgagtaaac cctcaaattt gtctagtagt aattgagaat ttcaatgcac aataacaaac    1440
tgttgcttcc aacccgcttc atcatcactc tccctaatcc tacttctatt ctcctccttc    1500
ccctctgcct cgcgtctgtt cgctcctact cgcttccttg tctccaccta tgattacatg    1560
ataccttccc ctcgggggggg ggggccgggc cacatatccc ccccaaagtg              1610
```

<210> SEQ ID NO 20
<211> LENGTH: 316
<212> TYPE: PRT
<213> ORGANISM: Glycine max

<400> SEQUENCE: 20

```
Met Gly Lys Gly Gly Met Ser Ile Asp Glu His Gly Glu Gly Lys Glu
 1               5                  10                  15

Glu Asn Met Ala Ala Trp Leu Val Gly Met Asn Thr Leu Lys Ile Gln
            20                  25                  30

Pro Phe Lys Leu Pro Thr Leu Gly Pro His Asp Val Arg Val Arg Met
        35                  40                  45

Lys Ala Val Gly Ile Cys Gly Ser Asp Val His Tyr Leu Lys Thr Leu
    50                  55                  60

Arg Cys Ala His Phe Ile Val Lys Glu Pro Met Val Ile Gly His Glu
65                  70                  75                  80

Cys Ala Gly Ile Ile Glu Val Gly Ser Gln Val Lys Ser Leu Val
                85                  90                  95

Pro Gly Asp Arg Val Ala Ile Glu Pro Gly Ile Ser Cys Trp His Cys
            100                 105                 110

Asn His Cys Lys His Gly Arg Tyr Asn Leu Cys Asp Asp Met Lys Phe
        115                 120                 125

Phe Ala Thr Pro Pro Val His Gly Ser Leu Ala Asn Gln Ile Val His
    130                 135                 140

Pro Ala Asp Leu Cys Phe Lys Leu Pro Asp Asn Val Ser Leu Glu Glu
145                 150                 155                 160

Gly Ala Met Cys Glu Pro Leu Ser Val Gly Val His Ala Cys Arg Arg
                165                 170                 175

Ala Asn Ile Gly Pro Glu Thr Asn Val Leu Ile Met Gly Ala Gly Pro
            180                 185                 190

Ile Gly Leu Val Thr Met Leu Ala Ala Arg Ala Phe Gly Ala Pro Lys
        195                 200                 205

Thr Val Ile Val Asp Val Asp His Arg Leu Ser Val Ala Lys Ser
    210                 215                 220

Leu Gly Ala Asp Asp Ile Ile Lys Val Ser Thr Asn Ile Lys Asp Val
225                 230                 235                 240

Ala Glu Glu Val Val Gln Ile Gln Lys Val Met Gly Ala Gly Ile Asp
                245                 250                 255

Val Thr Phe Asp Cys Ala Gly Phe Asp Lys Thr Met Ser Pro Ala Leu
            260                 265                 270

Ser Ala Thr Gln Pro Gly Gly Lys Val Cys Leu Val Gly Met Gly His
        275                 280                 285

Ser Glu Met Thr Val Pro Leu Thr Pro Ser Cys Ser Lys Leu Tyr Trp
    290                 295                 300

Ile Phe Ile Thr Phe Leu Lys Ala Trp Ile Leu His
305                 310                 315
```

<210> SEQ ID NO 21
<211> LENGTH: 933

```
<212> TYPE: DNA
<213> ORGANISM: Triticum aestivum

<400> SEQUENCE: 21
gcacgaggcg gccgtggccg gcgaggggga gaacatggcg gcgtggctcg tggccaagaa      60
caccctcaag atcatgccct tcaagcttcc gccgctgggt ccttatgatg tgcgagtccg     120
gatgaaggcg gtgggcatct gcggcagcga cgtgcattac ctcaaggaga tgcgcattgc     180
gcatttcgtg gtgaaagagc cgatggtgat cgggcacgag tgcgctggca tcatcgagga     240
ggtgggcgac ggcgtgaagc acctcgccgt gggagaccgt gtggcgctgg agcccggcat     300
cagctgctgg cgctgcaggc actgcaaggg cggccgctac aacctctgcg acgacatgaa     360
gttcttcgcc accccacctt accatggatc acttgccgac cagattgtgc atccaggtga     420
cctgtgcttc aagcttccag acaacgtgag cctggaggag ggcgccatgt gcgagcccct     480
gagcgtgggg gtgcacgcct gccgccgagc cgacgtgggc gcggagaaga gcgtgctcat     540
catgggcgcc ggcccgatcg gcctggtcac catgctctcg gcgcgcgcct cggggcgcc     600
caggatcgtc atcgccgacg tcgacgacca ccgcctctcc gtggccaagt ccctcggcgc     660
ggacgccgtc gtgaaggtct ccggcaacac ggaggacctc gcggggggaga tcgagcgcat     720
ccaggcggcg atgggaggcg acatcgacgt gagcctggac tgcgccgggt tcagcaagac     780
gatgtcgacg gcgctggagg cgacgcggcc gggcgggagg gtgtgcctgg tggggatggg     840
gcacaacgag atgacggtgc cgctgacgtc ggcggcgatc cgggaggtgg acgtggtggg     900
gatcttccgt tacaaggaca cgtggccgct gtg                                  933

<210> SEQ ID NO 22
<211> LENGTH: 301
<212> TYPE: PRT
<213> ORGANISM: Triticum aestivum

<400> SEQUENCE: 22

Glu Asn Met Ala Ala Trp Leu Val Ala Lys Asn Thr Leu Lys Ile Met
  1               5                  10                  15
Pro Phe Lys Leu Pro Pro Leu Gly Pro Tyr Asp Val Arg Val Arg Met
             20                  25                  30
Lys Ala Val Gly Ile Cys Gly Ser Asp Val His Tyr Leu Lys Glu Met
         35                  40                  45
Arg Ile Ala His Phe Val Val Lys Glu Pro Met Val Ile Gly His Glu
     50                  55                  60
Cys Ala Gly Ile Ile Glu Glu Val Gly Asp Gly Val Lys His Leu Ala
 65                  70                  75                  80
Val Gly Asp Arg Val Ala Leu Glu Pro Gly Ile Ser Cys Trp Arg Cys
                 85                  90                  95
Arg His Cys Lys Gly Gly Arg Tyr Asn Leu Cys Asp Asp Met Lys Phe
            100                 105                 110
Phe Ala Thr Pro Pro Tyr His Gly Ser Leu Ala Asp Gln Ile Val His
        115                 120                 125
Pro Gly Asp Leu Cys Phe Lys Leu Pro Asp Asn Val Ser Leu Glu Glu
    130                 135                 140
Gly Ala Met Cys Glu Pro Leu Ser Val Gly Val His Ala Cys Arg Arg
145                 150                 155                 160
Ala Asp Val Gly Ala Glu Lys Ser Val Leu Ile Met Gly Ala Gly Pro
                165                 170                 175
Ile Gly Leu Val Thr Met Leu Ser Ala Arg Ala Phe Gly Ala Pro Arg
```

```
                    180             185             190
Ile Val Ile Ala Asp Val Asp His Arg Leu Ser Val Ala Lys Ser
            195             200             205
Leu Gly Ala Asp Ala Val Lys Val Ser Gly Asn Thr Glu Asp Leu
    210             215             220
Ala Gly Glu Ile Glu Arg Ile Gln Ala Ala Met Gly Gly Asp Ile Asp
225             230             235             240
Val Ser Leu Asp Cys Ala Gly Phe Ser Lys Thr Met Ser Thr Ala Leu
            245             250             255
Glu Ala Thr Arg Pro Gly Gly Arg Val Cys Leu Val Gly Met Gly His
            260             265             270
Asn Glu Met Thr Val Pro Leu Thr Ser Ala Ala Ile Arg Glu Val Asp
            275             280             285
Val Val Gly Ile Phe Arg Tyr Lys Asp Thr Trp Pro Leu
    290             295             300
```

<210> SEQ ID NO 23
<211> LENGTH: 320
<212> TYPE: PRT
<213> ORGANISM: Hordeum vulgare

<400> SEQUENCE: 23

```
Met Ala Ser Ala Lys Ala Thr Met Gly Gln Gly Glu Gln Asp His Phe
1               5               10              15
Val Leu Lys Ser Gly His Ala Met Pro Ala Val Gly Leu Gly Thr Trp
            20              25              30
Arg Ala Gly Ser Asp Thr Ala His Ser Val Arg Thr Ala Ile Thr Glu
        35              40              45
Ala Gly Tyr Arg His Val Asp Thr Ala Ala Glu Tyr Gly Val Glu Lys
    50              55              60
Glu Val Gly Lys Gly Leu Lys Ala Ala Met Glu Ala Gly Ile Asp Arg
65              70              75              80
Lys Asp Leu Phe Val Thr Ser Lys Ile Trp Cys Thr Asn Leu Ala Pro
            85              90              95
Glu Arg Val Arg Pro Ala Leu Glu Asn Thr Leu Lys Asp Leu Gln Leu
        100             105             110
Asp Tyr Ile Asp Leu Tyr His Ile His Trp Pro Phe Arg Leu Lys Asp
    115             120             125
Gly Ala His Met Pro Pro Glu Ala Gly Glu Val Leu Glu Phe Asp Met
130             135             140
Glu Gly Val Trp Lys Glu Met Glu Asn Leu Val Lys Asp Gly Leu Val
145             150             155             160
Lys Asp Ile Gly Val Cys Asn Tyr Thr Val Thr Lys Leu Asn Arg Leu
            165             170             175
Leu Arg Ser Ala Lys Ile Pro Pro Ala Val Cys Gln Met Glu Met His
        180             185             190
Pro Gly Trp Lys Asn Asp Lys Ile Phe Glu Ala Cys Lys Lys His Gly
    195             200             205
Ile His Val Thr Ala Tyr Ser Pro Leu Gly Ser Ser Glu Lys Asn Leu
    210             215             220
Ala His Asp Pro Val Val Glu Lys Val Ala Asn Lys Leu Asn Lys Thr
225             230             235             240
Pro Gly Gln Val Leu Ile Lys Trp Ala Leu Gln Arg Gly Thr Ser Val
            245             250             255
```

```
Ile Pro Lys Ser Ser Lys Asp Glu Arg Ile Lys Glu Asn Ile Gln Val
            260                 265                 270

Phe Gly Trp Glu Ile Pro Glu Glu Asp Phe Lys Val Leu Cys Ser Ile
        275                 280                 285

Lys Asp Glu Lys Arg Val Leu Thr Gly Glu Glu Leu Phe Val Asn Lys
    290                 295                 300

Thr His Gly Pro Tyr Arg Ser Ala Ala Asp Val Trp Asp His Glu Asn
305                 310                 315                 320

<210> SEQ ID NO 24
<211> LENGTH: 319
<212> TYPE: PRT
<213> ORGANISM: Avena fatua

<400> SEQUENCE: 24

Met Ala Ser Ala Lys Ala Met Gly Gln Gly Glu Gln Asp Arg Phe Val
  1               5                  10                  15

Leu Lys Ser Gly His Ala Ile Pro Ala Val Gly Leu Gly Thr Trp Arg
             20                  25                  30

Ala Gly Ser Asp Thr Ala His Ser Val Gln Thr Ala Ile Thr Glu Ala
         35                  40                  45

Gly Tyr Arg His Val Asp Thr Ala Ala Gln Tyr Gly Ile Glu Lys Glu
     50                  55                  60

Val Asp Lys Gly Leu Lys Ala Ala Met Glu Ala Gly Ile Asp Arg Lys
 65                  70                  75                  80

Asp Leu Phe Val Thr Ser Lys Ile Trp Arg Thr Asn Leu Ala Pro Glu
                 85                  90                  95

Arg Ala Arg Pro Ala Leu Glu Asn Thr Leu Lys Asp Leu Gln Leu Asp
            100                 105                 110

Tyr Ile Asp Leu Tyr Leu Ile His Trp Pro Phe Arg Leu Lys Asp Gly
        115                 120                 125

Ala His Gln Pro Pro Glu Ala Gly Glu Val Leu Glu Phe Asp Met Glu
    130                 135                 140

Gly Val Trp Lys Glu Met Glu Lys Leu Val Lys Asp Gly Leu Val Lys
145                 150                 155                 160

Asp Ile Asp Val Cys Asn Phe Thr Val Thr Lys Leu Asn Arg Leu Leu
                165                 170                 175

Arg Ser Ala Asn Ile Pro Pro Ala Val Cys Gln Met Glu Met His Pro
            180                 185                 190

Gly Trp Lys Asn Asp Lys Ile Phe Glu Ala Cys Lys Lys His Gly Ile
        195                 200                 205

His Val Thr Ala Tyr Ser Pro Leu Gly Ser Ser Glu Lys Asn Leu Val
    210                 215                 220

His Asp Pro Val Glu Lys Val Ala Asn Lys Leu Asn Lys Thr Pro
225                 230                 235                 240

Gly Gln Val Leu Ile Lys Trp Ala Leu Gln Arg Gly Thr Ser Val Ile
                245                 250                 255

Pro Lys Ser Ser Lys Asp Glu Arg Ile Lys Glu Asn Ile Gln Ala Phe
            260                 265                 270

Gly Trp Glu Ile Pro Glu Asp Phe Gln Val Leu Cys Ser Ile Lys
        275                 280                 285

Asp Glu Lys Arg Val Leu Thr Gly Glu Glu Leu Phe Val Asn Lys Thr
    290                 295                 300

His Gly Pro Tyr Lys Ser Ala Ser Glu Val Trp Asp His Glu Asn
305                 310                 315
```

<210> SEQ ID NO 25
<211> LENGTH: 313
<212> TYPE: PRT
<213> ORGANISM: Medicago sativa

<400> SEQUENCE: 25

Met Ala Thr Ala Ile Lys Phe Phe Gln Leu Asn Thr Gly Ala Lys Ile
1               5                   10                  15

Pro Ser Val Gly Leu Gly Thr Trp Gln Ala Glu Pro Gly Val Val Ala
            20                  25                  30

Lys Ala Val Thr Thr Ala Val Gln Val Gly Tyr Arg His Ile Asp Cys
        35                  40                  45

Ala Glu Ala Tyr Lys Asn Gln Ser Glu Ile Gly Ser Ala Leu Lys Lys
    50                  55                  60

Leu Cys Glu Asp Gly Val Val Lys Arg Glu Glu Leu Trp Ile Thr Ser
65                  70                  75                  80

Lys Leu Trp Cys Ser Asp His His Pro Glu Asp Val Pro Lys Ala Leu
                85                  90                  95

Asp Lys Thr Leu Asn Asp Leu Gln Leu Asp Tyr Leu Asp Leu Tyr Leu
            100                 105                 110

Ile His Trp Pro Val Ser Met Lys Arg Gly Thr Gly Glu Phe Met Gly
        115                 120                 125

Glu Asn Leu Asp His Ala Asp Ile Pro Ser Thr Trp Lys Ala Leu Gly
    130                 135                 140

Ala Leu Tyr Asp Ser Gly Lys Ala Lys Ala Ile Gly Val Ser Asn Phe
145                 150                 155                 160

Ser Thr Lys Lys Leu Gln Asp Leu Leu Asp Val Ala Arg Val Pro Pro
                165                 170                 175

Ala Val Asn Gln Val Glu Leu His Pro Gly Trp Gln Gln Ala Lys Leu
            180                 185                 190

His Ala Phe Cys Glu Ser Lys Gly Ile His Leu Ser Gly Tyr Ser Pro
        195                 200                 205

Leu Gly Ser Pro Gly Val Leu Lys Ser Asp Ile Leu Lys Asn Pro Val
    210                 215                 220

Val Lys Glu Ile Ala Glu Lys Leu Gly Lys Thr Pro Gly Gln Val Ala
225                 230                 235                 240

Leu Arg Trp Gly Leu Gln Ala Gly His Ser Val Leu Pro Lys Ser Thr
                245                 250                 255

Asn Glu Ala Arg Ile Lys Lys Asn Leu Asp Val Tyr Asp Trp Ser Ile
            260                 265                 270

Pro Glu Asp Leu Phe Pro Lys Phe Ser Glu Ile Lys Gln Asp Lys Leu
        275                 280                 285

Ile Lys Gly Thr Phe Phe Val Asn Asp Thr Tyr Gly Ala Phe Arg Thr
    290                 295                 300

Ile Glu Glu Leu Trp Asp Gly Glu Val
305                 310

<210> SEQ ID NO 26
<211> LENGTH: 309
<212> TYPE: PRT
<213> ORGANISM: Apium graveolens

<400> SEQUENCE: 26

Met Ala Ile Thr Leu Asn Ser Gly Phe Lys Met Pro Val Leu Gly Leu
1               5                   10                  15

-continued

```
Gly Val Trp Arg Met Asp Arg Asn Glu Ile Lys Asn Leu Leu Leu Ser
            20                  25                  30

Ala Ile Asn Leu Gly Tyr Arg His Phe Asp Cys Ala Ala Asp Tyr Lys
        35                  40                  45

Asn Glu Leu Glu Val Gly Glu Ala Phe Lys Glu Ala Phe Asp Thr Asp
    50                  55                  60

Leu Val Lys Arg Glu Asp Leu Phe Ile Thr Thr Lys Leu Trp Asn Ser
65                  70                  75                  80

Asp His Gly His Val Ile Glu Ala Cys Lys Asn Ser Leu Lys Lys Leu
                85                  90                  95

Gln Leu Glu Tyr Leu Asp Leu Tyr Leu Ile His Phe Pro Met Ala Ser
            100                 105                 110

Lys His Ser Gly Ile Gly Thr Thr Arg Ser Ile Leu Asp Asp Glu Gly
        115                 120                 125

Val Trp Glu Val Asp Ala Thr Ile Ser Leu Glu Ala Thr Trp His Glu
    130                 135                 140

Met Glu Lys Leu Val Glu Met Gly Leu Val Arg Ser Ile Gly Ile Ser
145                 150                 155                 160

Asn Tyr Asp Val Tyr Leu Thr Arg Asp Ile Leu Ser Tyr Ser Lys Ile
                165                 170                 175

Lys Pro Ala Val Asn Gln Ile Glu Thr His Pro Tyr Phe Gln Arg Asp
            180                 185                 190

Ser Leu Ile Lys Phe Cys Gln Leu Tyr Gly Ile Ala Ile Thr Ala His
        195                 200                 205

Thr Pro Leu Gly Gly Ala Leu Ala Asn Thr Glu Arg Phe Gly Ser Val
    210                 215                 220

Ser Cys Leu Asp Asp Pro Val Leu Lys Leu Ser Asp Lys His Asn
225                 230                 235                 240

Lys Ser Pro Ala Gln Ile Val Leu Arg Trp Gly Val Gln Arg Asn Thr
                245                 250                 255

Ile Val Ile Pro Lys Ser Ser Lys Thr Lys Arg Leu Glu Glu Asn Ile
            260                 265                 270

Asn Ile Phe Asp Phe Glu Leu Ser Lys Glu Asp Met Glu Leu Ile Lys
        275                 280                 285

Thr Met Glu Arg Asn Gln Arg Ser Asn Thr Pro Ala Lys Ala Trp Gly
    290                 295                 300

Ile Asp Val Tyr Ala
305
```

<210> SEQ ID NO 27
<211> LENGTH: 371
<212> TYPE: PRT
<213> ORGANISM: Malus domestica

<400> SEQUENCE: 27

```
Met Gly Lys Gly Gly Met Ser Asp Gly Asp His Ala Asp Arg Cys Cys
1               5                   10                  15

Gly Glu Ala Ile Asn Gly Asp Val Gln Gln Glu Asn Met Ala Ala Trp
            20                  25                  30

Leu Leu Gly Val Lys Asn Leu Lys Ile Gln Pro Tyr Lys Leu Pro Asn
        35                  40                  45

Leu Gly Pro His Asp Val Arg Val Arg Leu Arg Ala Val Gly Ile Cys
    50                  55                  60

Gly Ser Asp Val His His Phe Lys Asn Met Arg Cys Val Asp Phe Ile
```

-continued

```
             65                  70                  75                  80
Val Lys Glu Pro Met Val Ile Gly His Glu Cys Ala Gly Ile Ile Glu
                    85                  90                  95
Glu Val Gly Ser Glu Val Glu His Leu Val Pro Gly Asp Arg Val Ala
                100                 105                 110
Leu Glu Pro Gly Ile Ser Cys Lys Arg Cys Asn Leu Cys Lys Gln Gly
                115                 120                 125
Arg Tyr Asn Leu Cys Arg Lys Met Lys Phe Phe Gly Ser Pro Pro Asn
            130                 135                 140
Asn Gly Cys Leu Ala Asn Gln Val Val His Pro Gly Asp Leu Cys Phe
145                 150                 155                 160
Lys Leu Pro Asp Asn Val Ser Leu Glu Glu Gly Ala Met Cys Glu Pro
                165                 170                 175
Leu Ser Val Gly Ile His Ala Cys Arg Arg Ala Asn Val Cys Gln Glu
                180                 185                 190
Thr Asn Val Leu Val Gly Ala Gly Pro Ile Gly Leu Val Thr Leu
            195                 200                 205
Leu Ala Ala Arg Ala Phe Gly Ala Pro Arg Ile Val Ile Ala Asp Val
    210                 215                 220
Asn Asp Glu Arg Leu Leu Ile Ala Lys Ser Leu Gly Ala Asp Ala Val
225                 230                 235                 240
Val Lys Val Ser Thr Asn Ile Glu Asp Val Ala Glu Val Ala Lys
                245                 250                 255
Ile Gln Lys Val Leu Glu Asn Gly Val Asp Val Thr Phe Asp Cys Ala
                260                 265                 270
Gly Phe Asn Lys Thr Ile Thr Thr Ala Leu Ser Ala Thr Arg Pro Gly
            275                 280                 285
Gly Lys Val Cys Leu Val Gly Met Gly Gln Arg Glu Met Thr Leu Pro
            290                 295                 300
Leu Ala Thr Arg Glu Ile Asp Val Ile Gly Ile Phe Arg Tyr Gln Asn
305                 310                 315                 320
Thr Trp Pro Leu Cys Leu Glu Phe Leu Arg Ser Gly Lys Ile Asp Val
                325                 330                 335
Lys Pro Leu Ile Thr His Arg Phe Gly Phe Ser Gln Lys Glu Val Glu
                340                 345                 350
Glu Ala Phe Glu Thr Ser Ala Arg Gly Gly Asn Ala Ile Lys Val Met
            355                 360                 365
Phe Asn Leu
    370
```